United States Patent [19]

Marhold et al.

[11] 4,225,731
[45] Sep. 30, 1980

[54] PROCESS FOR THE PREPARATION OF TRIFLUOROMETHYLPHENOLS

[75] Inventors: Albrecht Marhold, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 924,474

[22] Filed: Jul. 13, 1978

[30] Foreign Application Priority Data

Jul. 26, 1977 [DE] Fed. Rep. of Germany ....... 2733682

[51] Int. Cl.$^2$ .............................................. C07C 39/02
[52] U.S. Cl. ..................................... 568/775; 568/778
[58] Field of Search ............... 568/776, 775, 778, 629, 568/777

[56] References Cited

U.S. PATENT DOCUMENTS

| | | | |
|---|---|---|---|
| 2,872,461 | 2/1959 | Mattner | 568/777 |
| 2,950,325 | 8/1960 | Britton et al. | 568/778 |
| 3,351,670 | 11/1967 | Belf | 568/778 |

FOREIGN PATENT DOCUMENTS

| | | | |
|---|---|---|---|
| 1469596 | 1/1967 | France | 568/778 |
| 718779 | 11/1954 | United Kingdom | 568/777 |

OTHER PUBLICATIONS

Dehmlow "Chemtech" (1975), pp. 210–217.
Wall, et al., "J. of Research, N.B.S.," vol. 67A (1963), pp. 481–496.

*Primary Examiner*—Werren B. Lone
*Attorney, Agent, or Firm*—Sprung, Felfe, Horn, Lynch & Kramer

[57] ABSTRACT

A process for the preparation of a trifluoromethylphenol or the corresponding alkoxy compound which comprises contacting a halogenobenzotrifluoride of the formula

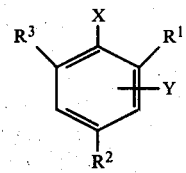

in which
X denotes halogen,
$R^1$, $R^2$ and $R^3$ denote hydrogen, trifluoromethyl or a substituent which promotes the replacement of X by a hydroxyl group and
Y denotes hydrogen, a halogen or alkoxy, at least one of the substituents $R^1$, $R^2$ and $R^3$ representing a trifluoromethyl group and at least one of them representing a substituent which promotes the replacement of the radical X by a hydroxyl group, with an excess aqueous alkali metal hydroxide in an alcoholic solution in the presence of a quaternary onium salt.

11 Claims, No Drawings

PROCESS FOR THE PREPARATION OF TRIFLUOROMETHYLPHENOLS

The invention relates to a process for the preparation of phenols with a trifluoromethyl group.

It is known to prepare, for example, 2-nitro-4-trifluoromethylphenol by reacting 4-chloro-3-nitro-benzotrifluoride with sodium hydroxide solution in dimethylsulphoxide (J. org. Chem. 36, 242 (1971)).

Trifluoromethylphenols are obtained by another process by splitting the corresponding methoxy compounds with pyridine hydrochloride at 210° C. (J. org. Chem. 27, 4,660 (1962). In this process, the methoxy compounds are prepared from chloronitrobenzotrifluorides in a prior process stage.

A process has been found for the preparation of trifluoromethylphenols in which compounds of the formula

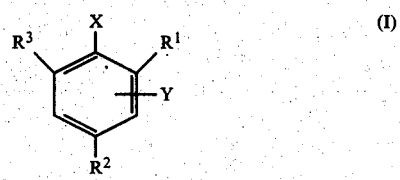

in which
X denotes halogen,
$R^1$, $R^2$ and $R^3$ denote hydrogen, trifluoromethyl or a substituent which promotes the replacement of X by the hydroxyl group and
Y denotes hydrogen, a halogen or alkoxy, at least one of the substituents $R^1$, $R^2$ and $R^3$ representing a trifluoromethyl group and at least one of them representing a substituent which promotes the replacement of the radical X by a hydroxyl group,
are reacted with excess aqueous alkali metal hydroxide in alcoholic solution in the presence of quaternary onium salts.

Halogens (X) can be fluorine, chlorine, bromine or iodine, preferably fluorine or chlorine.

Examples of possible substituents $R^1$, $R^2$ or $R^3$ which promote the replacement of the radical X by a hydroxyl group are second order substituents (Beyer, Lehrbuch der organ. Chemie (Textbook of organic Chemistry), Leipzig 1962, page 373). Examples which may be mentioned are: the nitro group, the alkylsulphonyl group, the alkyl radical of which can be, a straight-chain or branched lower alkyl radical with 1-8 carbon atoms, such as, for example, methyl, ethyl, propyl, isopropyl or isomeric butyl, hexyl or octyl, the arylsulphone group, the aryl radical of which can be phenyl or a phenyl which is substituted, for example by chlorine or methyl, the trifluoromethyl group, the carboxyl group or the carboxylic acid ester group, the alcohol component (supplying the esterfunction) of which can be a straight-chain or branched lower aliphatic alcohol with 1-8 carbon atoms, such as, for example, methanol, ethanol, propanol, isopropanol or the isomeric butanols, hexanols or octanols.

Examples of the halogen atom (Y) which may be mentioned are fluorine, chlorine, bromine or iodine, preferably chlorine or bromine.

As the alkoxy group (Y) preferably contains alkyl radicals with 1 to 4 carbon atoms, for example the methyl, ethyl, propyl, isopropyl, butyl or tert.-butyl radical.

Preferred compounds of the formula (I) which may be mentioned are compounds of the formula II

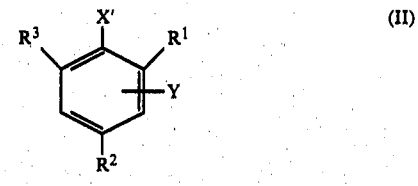

in which
X' denotes a fluorine atom or a chlorine atom and the radicals $R^1$, $R^2$ and $R^3$ have the abovementioned meaning.

Compounds of the formula I are known and can be prepared by nitrating chloro-trifluoromethylbenzene with nitric acid/sulphuric acid (J. org. Chem. 26, 2,707 (1961)).

The following compounds of the formula (I) may be mentioned as examples: 4-chloro-3-nitro-benzotrifluoride, 2-chloro-5-nitro-benzotrifluoride, 3,4-dichloro-5-nitro-benzotrifluoride, 2,3-dichloro-5-nitro-benzotrifluoride, 2,4-dichloro-5-nitro-benzotrifluoride, 6-chloro-3-nitro-5-trifluoromethylbenzoic acid, 2-chloro-3-nitro-5-trifluoromethyl-benzoic acid, 4-bromo-3-nitro-benzotrifluoride, 2-bromo-5-nitro-benzotrifluoride, 2-chloro-3-methoxy-5-nitro-benzotrifluoride and 2-methoxy-4-chloro-5-nitro-benzotrifluoride.

Alcohols with a lower unbranched or branched alkyl radical can be employed as solvents for the process according to the invention. Preferred alcohols which may be mentioned are those with an unbranched or branched alkyl radical which has 1 to 4 carbon atoms, such as methanol, ethanol, propanol, isopropanol, the various isomeric butanols, glycol and glycol monomethyl ether.

The amount of solvent can vary within wide limits; thus, for example, 1 to 20 parts by weight, preferably 2 to 8 parts by weight, of solvent can be employed per 1 part by weight a compound of the formula (I).

Sodium hydroxide or potassium hydroxide are preferably employed as alkali metal hydroxides for the process according to the invention. In general, they are used in the form of their aqueous solutions, which contains, for example, 30–50% by weight of alkali metal hydroxide. However, the sodium hydroxide or potassium hydroxide can also be introduced into the aqueous alcoholic solution in the solid form. The alkali metal hydroxides are generally employed in excess. It is particularly advantageous to use at least about three times the molar about thereof based on the reaction of the halogen atom to give the phenolic hydroxyl group.

The water content of the reaction solution can vary within the wide limits. In general, it can be about 20 to 25% by weight.

Onium salts of the formula

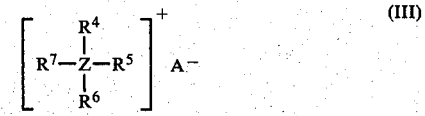

in which

Z represents an element of main group 5 of the periodic system,

R⁴ to R⁷ are identical or different and denote optionally substituted alkyl, cycloalkyl, aralkyl or aryl, or two of the radicals R⁴ to R⁷, together with the central atom Z and optionally further heteroatoms, form a heterocyclic ring, the radicals R⁴ to R⁷ together containing at least 6 carbon atoms, and A denotes an inorganic or organic anion which is inert under the conditions of the process according to the invention, can be employed for the process according to the invention.

Elements of main group 5 of the periodic system (according to Mendeleev) which may be mentioned are: nitrogen, phosphorus, arsenic, antimony or bismuth.

The radicals R⁴ to R⁷ can be low-molecular or high-molecular organic radicals.

Low-molecular radicals which may be mentioned are optionally substituted alkyl radicals, cycloalkyl radicals, aralkyl radicals or aryl radicals. Two of the radicals R⁴ to R⁷ can also form, together with the central atom Z and optionally further hetero-atoms, a heterocyclic ring.

The optionally substituted or branched alkyl radicals can be, above all, those with 1–8 carbon atoms, preferably with 1–12 carbon atoms, such as of the methyl and ethyl radicals and the isomeric propyl, butyl, octyl, decyl or dodecyl radicals.

The cycloalkyl radicals can be cyclopentyl and, in particular, cyclohexyl radicals which are optionally substituted by $C_1$–$C_4$-alkyl radicals.

The aralkyl radicals can be benzyl radicals which are optionally substituted by $C_1$–$C_4$-alkyl radicals, methoxy groups or halogen atoms.

The aryl radicals can be phenyl radicals which are optionally substituted by $C_1$–$C_4$-alkyl radicals, methoxy groups, ethoxy groups or halogen atoms.

In the case of a heterocyclic ring which two adjacent radicals R⁴ to R⁷ can form, together with the central atom Z and optionally with further hetero-atoms, preferred possible further hetero-atoms are oxygen, nitrogen or sulphur.

Preferred heterocyclic rings which may be mentioned are the 5-membered and 6-membered heterocyclic rings, for example the pyrrolidine ring, the piperidine or the morpholine ring.

An example which may be mentioned of a polymeric organic radical for one of the radicals R⁴ to R⁷ is a polystyrene radical which is optionally crosslinked by divinylbenzene.

The total number of the carbon atoms of all the radicals R⁴ to R⁷ is at least six for the process according to the invention. The maximum number of all the carbon atoms can be very high, for example in the case of a polymeric organic radical. The preferred total number of the carbon atoms of all the low-molecular radicals R⁴ to R⁷ is 8 to 25.

Preferred anions A are the chloride, bromide and hydroxide anion.

Preferred onium salts for the process according to the invention are quaternary ammonium or phosphonium salts of the formula

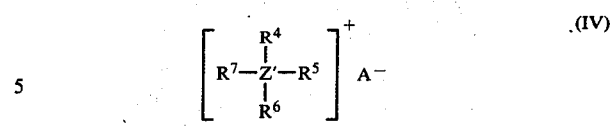

in which

Z' denotes nitrogen or phosphorus and

R⁴ to R⁷ and A have the meaning indicated above.

Examples of the preferred quaternary ammonium or phosphonium salts are: tetraethylammonium chloride, tetrabutylammonium bromide, trethyl-benzyl-ammonium hydroxide, benzyldimethyl-dodecyl-ammonium chloride, dibutyl-piperidinium bromide, methyl-trioctylammonium chloride, dimethyl-benzyl-phenyl-ammonium chloride, methyl-butyl-piperidinium bromide, benzyl-methyl-piperidinium hydroxide, triethyl-phenyl-ammonium chloride, dodecyl-trimethyl-ammonium hydroxide, cyclohexyldodecyl-dimethyl-ammonium chloride, methyl-ethyl-piperidinium bromide, triphenyl-benzyl-phosphonium bromide, tetrabutyl-phosphonium chloride and tributyl-benzyl-phosphonium chloride.

Quaternary ammonium compounds in which one of the radicals R⁴ to R⁷ is a polymeric radical can be, for example, ion exchangers which are based on styrene and, in general, 2 mol% of divinylbenzene as a cross-linking agent and which carry quaternary ammonium groups.

The amounts of the quaternary onium salt employed can vary from 1 to 20% by weight and in general are about 5 to 10% by weight, relative to the starting compound.

The quaternary onium salts mentioned are known as phase transfer catalysts in multi-phase systems and can be prepared by known processes (Houben-Weyl, 4th edition, Stuttgart 1958, volume XI, 2, page 587 and volume XIV, 2. page 750).

The process according to the invention can be carried out in a temperature range from about 0° to about 80° C., preferably from about 50° to 75° C.

The process according to the invention can be illustrated by the following equation:

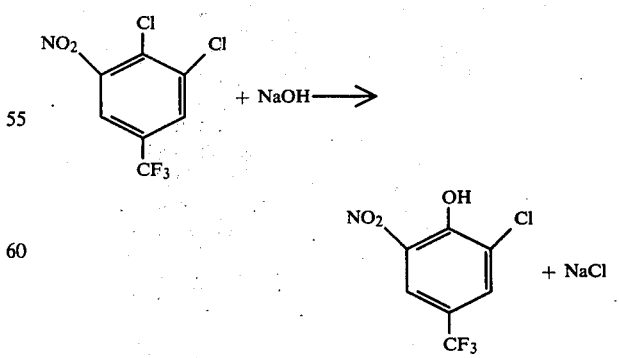

In a particular embodiment of the process according to the invention, intermediate products, for example alkoxy compounds of the formula

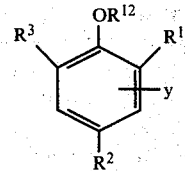

(V)

in which
the radicals $R^1$, $R^2$, $R^3$ and Y have the meaning indicated above and
$R^{12}$ is a lower unbranched or branched alkyl radical, can be isolated.

The alkyl radical $R^{12}$ of these alkoxy compounds can be determined by the alcohol used as the solvent. Thus, if methanol is used, a methoxy compound is obtained.

Such alkoxy compounds are known (J. Org. Chem. 26, 2,707 (1961)) and can be prepared, for example, by reaction of an organically bonded halogen atom with sodium methylate or with methanolic potassium hydroxide.

In the process according to the invention, these alkoxy compounds can be isolated if the process is carried out in the temperature range from about 15° to 35° C.

The alkoxy compounds can be isolated as intermediate products of the process according to the invention if the process is carried out at low temperatures.

The process according to the invention can be carried out, for example, as follows:

The starting compound, the solvent and the catalyst are initially introduced into the reaction vessel and the alkali metal hydroxide, for example as the aqueous solution, is added dropwise, whilst stirring. The temperature then increases; the rate of dropwise addition is regulated so that the desired reaction temperature is not exceeded. After the addition has ended, the mixture is further stirred at the reaction temperature for some hours. The phenol is present in the form of its alkali metal salt and can be obtained in the customary manner by acidification with a mineral acid. It can now be separated off by phase separation (in the case of liquids), by filtration (in the case of solid products), by extraction from the reaction mixture or by steam distillation.

Compared with the known processes for the preparation of trifluoromethylphenols, the process according to the invention has the advantage of being simple to carry out and of leading to the desired phenols in one stage.

The quaternary onium salts of the formula (IV) are known as phase transfer catalysts in systems with two liquid phases which are immiscible with one another (DT-OS (German Published Specification) No. 2,634,419).

The process according to the invention, however, is carried out with quaternary onium compounds in a system with only one liquid phase.

Trifluoromethylphenols of the formula

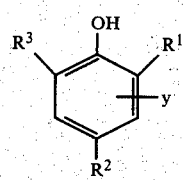

(VI)

in which the radicals $R^1$, $R^2$, $R^3$ and y have the meaning indicated above, can be prepared by the process according to the invention.

The trifluoromethylphenols of the formula

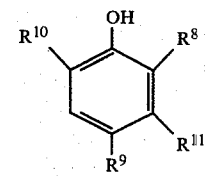

(VII)

in which
$R^8$ denotes trifluoromethyl, chlorine or hydrogen,
$R^9$ denotes trifluoromethyl, nitro or chlorine,
$R^{10}$ denotes nitro, chlorine or carboxyl and
$R^{11}$ denotes methoxy or hydrogen, one of the substituents $R^8$ and $R^9$ representing a trifluoromethyl group and at most one of the substituents $R^8$ and $R^{11}$ being hydrogen,
are new.

Examples of compounds of the formula (VII) which may be mentioned are: 2-chloro-4-trifluoromethyl-6-nitro-phenol, 2-chloro-6-trifluoromethyl-4-nitro-phenol, 4-chloro-2-trifluoromethyl-6-nitro-phenol, 3-methoxy-4-trifluoromethyl-6-nitrophenol and 5-nitro-3-trifluoromethyl-salicyclic acid.

The trifluoromethylphenols, in particular the new trifluoromethylphenols, are intermediate products for the preparation of herbicides (see DT-OS (German Published Specification) No. 2,311,638). For example, a trifluoromethylphenol of the formula VI can be reacted with p-nitrochlorobenzene in the presence of potassium methylate to yield trifluoromethyl-nitrodiphenyl ether which is advantageously applicable for weeds controlling in cotton, soybeans, peanuts, beans, peas, maize, wheat and other corn.

The trifluoromethylphenols are also intermediate products for the preparation of substituted dihydro-dibenzo-oxozepines which are useful as tranquilizers (see DT-OS (German Published Specification) No. 1,944,335). For example, 2-nitro-4-trifluoromethyl-phenol is reacted with hydrogen to reduce the nitro to the amino group and then reacted with formic acid to yield the corresponding formic acid anilide. The later is reacted with o-bromo-benzylbromide to yield 2-(o-bromo-benzyloxy)-4-trifluoro-methyl-formyl-aniline which can be cyclizated in the presence of potassium carbonate and copper powder to the dihydro-dibenzo-oxoazepine.

EXAMPLE 1

400 ml of methanol, 20 g of benzyldimethyl-dodecylammonium chloride and 180 g of 4-chloro-3-nitro-benzotrifluoride are initially introduced into the reaction flask, whilst stirring, and 400 g of 50% strength sodium hydroxide solution are then added dropwise. The temperature rises to about 70° C. if the addition is carried out in the course of about 20 minutes. The mixture is then stirred at 65° C. for a further 4 hours and subsequently cooled by adding ice, and the pH is adjusted to 3 with concentrated hydrochloric acid. The phenol is driven over with steam and the phases are separated in the receiver by adding about 50 ml of concentrated hydrochloric acid.

156 g of 2-nitro-4-trifluoromethylphenol are obtained with a purity of more than 98.5%, according to analysis by gas chromatography, which corresponds to a yield of 91% of theory. Boiling point: 92°–95° C. at 15 mm, $n_D^{20}$: 1.5020.

EXAMPLE 2

450 g of 2-chloro-5-nitro-benzotrifluoride in 1,250 ml of methanol and 35 g of tetraethylammonium chloride are initially introduced. 1,000 g of an aqueous, 50% strength potassium hydroxide solution are then added dropwise (1 hour), the temperature being kept at a maximum of 40° C. by cooling. About 30 minutes after the addition has ended, the mixture is heated to 80° C. for 6 hours, cooled and rendered acid with concentrated hydrochloric acid. The mixture is extracted several times with 300 ml of methylene chloride each time, and the organic phase is dried with sodium sulphate and freed from the solvent under reduced pressure. About 413 g of crude product, melting point: 90°–95° C., are obtained with a purity of about 95% according to analysis by gas chromatography. After recrystallisation from toluene, or distillation under 0.5 mm, pure 4-nitro-2-trifluoromethylphenol is obtained, melting point: 134° C.

EXAMPLE 3

50 g of 3,4-dichloro-5-nitro-benzotrifluoride and 5 g of benzyltriethylammonium bromide are initially introduced into 150 ml of methanol, and 100 g of 50% strength sodium hydroxide solution are added dropwise at 25° to 30° C. The mixture is then stirred at 65° C. for a further 4 hours and cooled, 100 ml of water are added and the mixture is rendered acid with sulphuric acid. The crude product is extracted with methylene chloride, the solution is dried and the methylene chloride is distilled off. The residue is subjected to fractional distillation and 35 g of 2-chloro-4-trifluoromethyl-6-nitrophenol with a boiling point of 74° to 76° C. under 0.25 mm are obtained. Melting point: 33°–34° C. from hexane. Yield: 77% of theory.

EXAMPLE 4

50 g of 2,3-dichloro-5-nitro-benzotrifluoride in 150 ml of methanol and 5 g of tetrabutylammonium chloride are initially introduced into the reaction vessel and 100 g of 50% strength sodium hydroxide solution are then added dropwise such that the temperature rises to a maximum of 50° C. The mixture is stirred at this temperature for a further 5 hours and then cooled and rendered acid with hydrochloric acid. The product is taken up in methylene chloride and, after drying with sodium sulphate, the methylene chloride solution is distilled. 33 g of 2-chloro-6-trifluoromethyl-4-nitrophenol, which has a melting point of 78° to 80° C., pass over at boiling point$_{0.1}$: 110° to 115° C. Yield: 73% of theory.

EXAMPLE 5

104 g of 2,4-dichloro-5-nitrobenzotrifluoride and 7 g of tetrabutylphosphonium chloride are initially introduced into 400 ml of methanol, and 400 g of 50% strength sodium hydroxide solution are added dropwise. The temperature is kept at a maximum of 70° C., and after the dropwise addition has ended, the mixture is stirred for a further 6 hours. The cooled mixture is rendered acid with hydrochloric acid and the product is then extracted with methylene chloride. After distilling off the solvent, the residue is recrystallised from isopropanol. 69 g of 3-methoxy-4-trifluoromethyl-6-nitrophenol with a melting point of 77° to 78° C. are obtained; the yield is 73% of theory.

EXAMPLE 6

45 g of 4-chloro-3-nitro-benzotrifluoride and 10 ml of 50% strength aqueous benzyldodecyldimethylammonium chloride are initially introduced into 150 ml of ethylene glycol monomethyl ether, and 100 g of 50% strength potassium hydroxide solution are added dropwise in the course of about 30 minutes, up to a temperature of 65° C. The mixture is then stirred at 65° C. for 6 hours and subsequently cooled and rendered acid with concentrated hydrochloric acid, and about 500 ml of distillate are driven over with steam. The organic phase is separated off and washed with 20 ml of dilute hydrochloric acid, and the organic phase is again separated off and dried with sodium sulphate. 38 g of 2-nitro-4-trifluoromethylphenol are obtained, which corresponds to a yield of 92% of theory.

EXAMPLE 7

If Example 6 is repeated and 150 ml of ethanol are used instead of ethylene glycol monomethyl ether, 39 g of 2-nitro-4-trifluoromethylphenol are obtained, which corresponds to 94% of theory.

EXAMPLE 8

27 g of 6-chloro-3-nitro-5-trifluoromethylbenzoic acid are dissolved in 100 ml of methanol, 1 g of trioctylmethylammonium chloride is added and 70 g of 50% strength sodium hydroxide solution are then added dropwise, whilst stirring, during which the temperature should not rise above 65° C. After the mixture has been stirred at 65° C. for a further 4 hours, it is cooled and water is added until everything has dissolved. The solution is then rendered acid by adding concentrated hydrochloric acid dropwise at 20° to 30° C., whereupon the product precipitates and is filtered off. The crude 5-nitro-3-trifluoromethyl-salicyclic acid is recrystallised from toluene, melting point: 171°–173° C., yield: 18 g; this corresponds to 72% of theory.

EXAMPLE 9

27 g of 2-chloro-3-nitro-5-trifluoromethyl-benzoic acid and 1 g of tetraethylammonium chloride are initially introduced into 200 ml of methanol, and 70 g of 50% strength sodium hydroxide solution are added dropwise, whilst stirring. The mixture is subsequently stirred at 65° C. for 5 hours, diluted with 300 ml of $H_2O$ and then rendered acid with hydrochloric acid. The solid product is filtered off and recrystallised from water. 16 g of 2-hydroxy-3-nitro-5-trifluoromethylbenzoic acid with the melting point: 166° to 168° C. are obtained.

EXAMPLE 10

45 g of 4-chloro-3-nitro-benzotrifluoride, dissolved in 150 ml of methanol, are initially introduced. 80 g of an ion exchanger resin containing quaternary ammonium groups are then introduced, the mixture is stirred for 10 minutes, 100 g of 50% strength sodium hydroxide solution are added dropwise, up to a maximum temperature of 70° C., and the mixture is stirred at 65° C. for 8 hours. After cooling the mixture, it is acidified with concentrated hydrochloric acid, the ion exchanger is filtered off and the crude product is distilled with steam. 27 g of 2-nitro-4-trifluoromethylphenol are obtained. $n_D^{20}$: 1.5003.

EXAMPLE 11

(A) 45 g of sodium hydroxide and 10 g of tetraethylammonium chloride in 200 g of methanol are initially introduced, 112.5 g of 2-chloro-5-nitro-benzotrifluoride are added dropwise at 25° to 30° C. and the mixture is then stirred at 30° C. for a further 5 hours. The mixture is then poured into 250 ml of water and extracted with methylene chloride. After evaporating off the solvent, the compound is recrystallised from isopropanol. 67 g of 2-methoxy-5-nitro-benzotrifluoride with a melting point of 70° to 74° C. are obtained.

(B) 67 g of 2-methoxy-5-nitro-benzotrifluoride are dissolved in 150 ml of methanol and first 8 g of tetraethylammonium chloride are added and then 150 g of 50% strength potassium hydroxide solution are added dropwise, up to a temperature of 70° C. The mixture is subsequently stirred at 70° C. for a further 8 hours, cooled, rendered acid and extracted with methylene chloride. After evaporating off the methylene chloride, 52 g of crude 4-nitro-2-trifluoromethyl-phenol, melting point: 90° to 94° C., remain, which can be purified by distillation.

What is claimed is:

1. A process for the preparation of a trifluoromethyl-phenol or the corresponding alkoxy compound which comprises contacting a halogenobenzotrifluoride of the formula

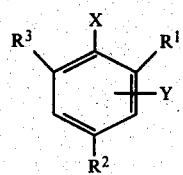

in which
X denotes halogen,
$R^1$, $R^2$ and $R^3$ denote hydrogen, trifluoromethyl or a substituent which promotes the replacement of X by a hydroxyl group and
Y denotes hydrogen, halogen or alkoxy, at least one of the substituents $R^1$, $R^2$ and $R^3$ representing a trifluoromethyl group and at least one of them representing a substituent which promotes the replacement of the radical X by a hydroxl group,
with an excess aqueous alkali metal hydroxide in an alcoholic solution in the presence of a quaternary onium salt of the formula

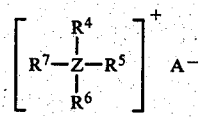

in which
Z denotes an atom of main group 5 of the periodic system,
$R^4$ to $R^7$ independently of one another denote alkyl, substituted alkyl, cycloalkyl, substituted cycloalkyl, aryl, or substituted aryl, of two of the radicals $R^4$ to $R^7$, together with the central atom Z which can additionally contain additional hetero-atoms, form a heterocyclic ring, the radicals $R^4$ to $R^7$ together containing at least 6 carbon atoms, and A denotes a chloride, bromide or hydroxide anion, at a temperature of from 0° to 80° C.

2. A process according to claim 1 wherein the quaternary onium saltis an quaternary ammonium or quaternary phosphonium salt, the substituents of which contain a total of 8 to 25 carbon atoms.

3. A process according to claim 1 wherein the quaternary onium salt is a quaternary ammonium salt and the quaternary ammonium salt is an ion exchanger which is based on styrene with 2 mol percent of divinylbenzene as cross-linking agent and the ion exchanger contain quaternary ammonium groups.

4. A process according to claim 1 wherein the quaternary onium salt is employed in an amount of 1 to 20% by weight based upon the weight of the halogenobenzotrifluoride.

5. A process according to claim 4 wherein the quaternary onium salt is employed in an amount of 5 to 10% by weight based upon the weight of the halogenobenzotrifluoride.

6. A process according to claim 1 wherein the alcoholic solvent is a lower unbranched or branched alkanol.

7. A process according to claim 1 wherein the alkali metal hydroxide is employed in at least about three times the molar amount based on the reaction of halogen atom to give the phenolic hydroxyl group.

8. A process according to claim 1 wherein the reaction is carried out at a temperature in the range of 15° to 35° C. whereby the corresponding alkoxy compound is formed.

9. A process according to claim 1 wherein the reaction is carried out at a temperature in the range of 50° to 75° C.

10. A process according to claim 1 wherein as a result of said reaction there is formed the corresponding alkali metal salt and alkali metal salt is converted to the corresponding phenol by contacting the same with an acid.

11. A process according to claim 1 wherein $R_4$ to $R_7$ independently of one another denote $C_1$ to $C_{18}$ alkyl, substituted $C_1$-$C_{18}$ alkyl, cyclopentyl or cyclohexyl, $C_1$-$C_4$-alkyl substituted cyclopentyl or cyclohexyl, phenyl, $C_1$-$C_4$-alkyl, methoxy, ethoxy or halo substituted phenol or two of the radicals $R_4$ to $R_7$, together with the central atom Z to form a heterocyclic ring selected from the group consisting of the pyrrolidine ring, the piperidine ring or the morpholine ring, the radicals $R_4$ to $R_7$ together containing at least 6 carbon atoms.

* * * * *